United States Patent [19]

Mallozzi et al.

[11] 4,143,275
[45] Mar. 6, 1979

[54] APPLYING RADIATION

[75] Inventors: Philip J. Mallozzi; Harold M. Epstein; Richard G. Jung; David C. Applebaum; Barry P. Fairand, all of Columbus; William J. Gallagher, Worthington, all of Ohio; Ronald L. Uecker, Wausau; Myron C. Muckerheide, Schofield, both of Wis.

[73] Assignee: Battelle Memorial Institute, Columbus, Ohio

[21] Appl. No.: 837,552

[22] Filed: Sep. 28, 1977

Related U.S. Application Data

[63] Continuation of Ser. No. 650,803, Jan. 20, 1979, abandoned, which is a continuation of Ser. No. 353,691, Apr. 23, 1973, abandoned.

[51] Int. Cl.$^2$ .............................................. G03B 41/00
[52] U.S. Cl. ..................................... 250/503; 250/505
[58] Field of Search .............. 250/493, 494, 495, 503, 250/505, 510; 350/96 R, 96 B

[56] References Cited

U.S. PATENT DOCUMENTS

| 2,766,385 | 10/1956 | Herrnring et al. | 250/505 |
|---|---|---|---|
| 2,819,404 | 1/1958 | Herrnring et al. | 250/505 |
| 3,388,314 | 6/1968 | Gould | 250/493 |
| 3,484,721 | 12/1969 | Bond et al. | 250/493 |
| 3,538,919 | 11/1970 | Meyer | 331/94.5 A |
| 3,617,939 | 11/1971 | Bond et al. | 250/493 |
| 3,628,021 | 12/1971 | MacDonald | 250/505 |

OTHER PUBLICATIONS

Pound et al., "Gravitational Red Shift in Nuclear Resonance," Physical Review letters, 3(9), 439–441 (1959).

Primary Examiner—Alfred E. Smith
Assistant Examiner—B. C. Anderson
Attorney, Agent, or Firm—Philip M. Dunson

[57] ABSTRACT

Method and apparatus for applying radiation by producing X-rays of a selected spectrum and intensity and directing them to a desired location. Radiant energy is directed from a laser onto a target to produce such X-rays at the target, which is so positioned adjacent to the desired location as to emit the X-rays toward the desired location; or such X-rays are produced in a region away from the desired location, and are channeled to the desired location.

The radiant energy directing means may be shaped (as with bends; adjustable, if desired) to circumvent any obstruction between the laser and the target. Similarly, the X-ray channeling means may be shaped (as with fixed or adjustable bends) to circumvent any obstruction between the region where the X-rays are produced and the desired location.

For producing a radiograph in a living organism the X-rays are provided in a short pulse to avoid any blurring of the radiograph from movement of or in the organism. For altering tissue in a living organism the selected spectrum and intensity are such as to affect substantially the tissue in a preselected volume without injuring nearby tissue. Typically, the selected spectrum comprises the range of about 0.1 to 100 keV, and the intensity is selected to provide about 100 to 1000 rads at the desired location.

The X-rays may be produced by stimulated emission thereof, typically in a single direction.

8 Claims, 6 Drawing Figures

U.S. Patent  Mar. 6, 1979  4,143,275
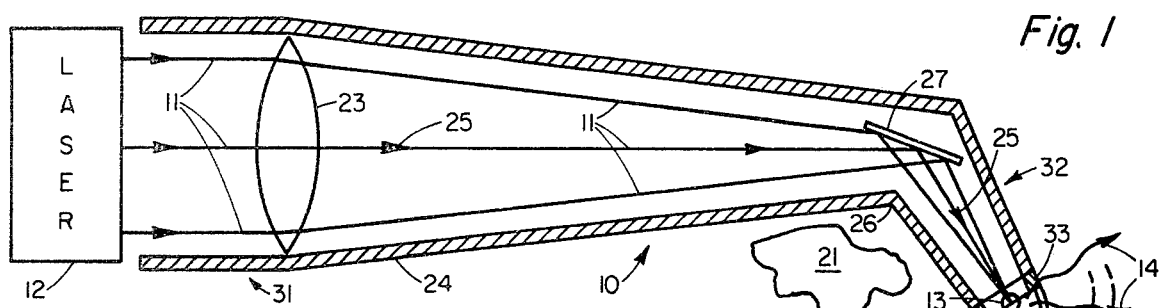
Fig. 1
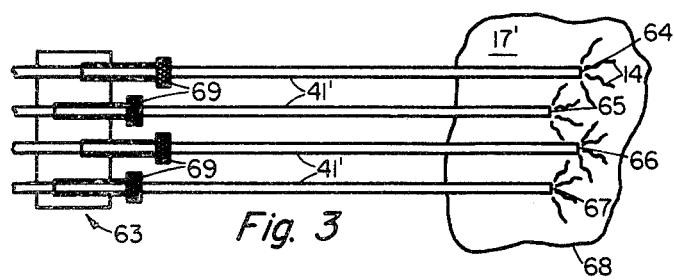
Fig. 3
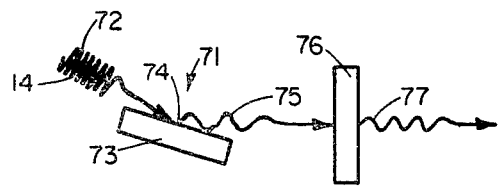
Fig. 4
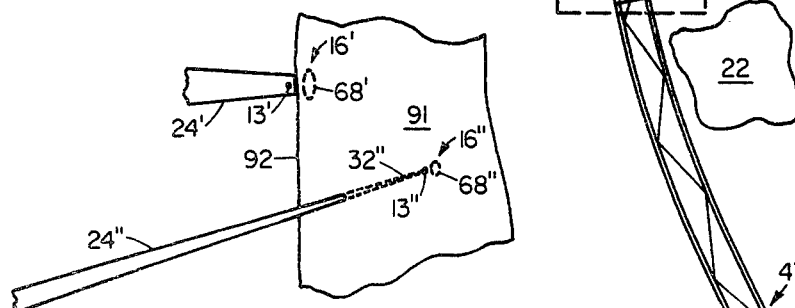
Fig. 5
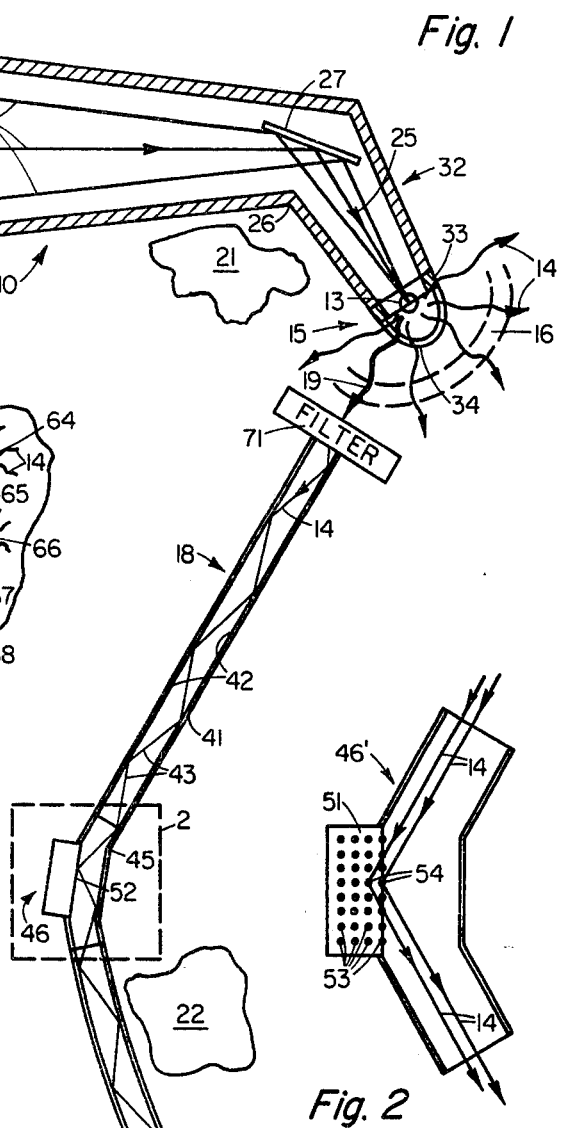
Fig. 2
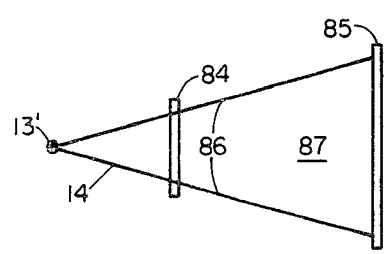
Fig. 6
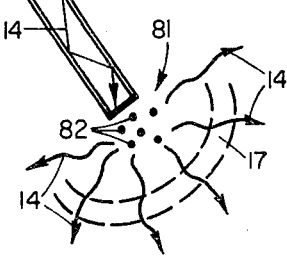

APPLYING RADIATION

This is a continuation of application Ser. No. 650,803, filed Jan. 20, 1976 abandoned, which is a continuation of application Ser. No. 353,691, filed Apr. 23, 1973 abandoned.

BACKGROUND

It is shown in the United States patent application of P. J. Mallozzi, H. M. Epstein, R. G. Jung, D. C. Applebaum, B. P. Fairand, and W. J. Gallagher, for Producing X-Rays, Ser. No. 319,756, filed Dec. 29, 1972 now U.S. Pat. No. 4,058,486, issued Nov. 15, 1977, that an intense point source of X-rays can be generated by focusing a laser beam onto a solid target. Neodymium laser light focused onto a solid slab target has been converted into X-rays with an efficiency greater than 25 percent, with several tens of joules of X-rays emanating from an essentially point source (about 100 microns diameter) in a nanosecond. The X-ray pattern produced with iron targets irradiated with about 100-joule laser pulses at a 45 degree angle of incidence is substantially omnidirectional. The conversion efficiency of greater than 25 percent refers to X-rays which are radiated away from the slab and pass perpendicularly through 3000 Angstroms of plastic (paraline) coated with 2000 Angstroms of aluminum. This conversion efficiency is thus a lower bound and refers only to the portion of the spectrum above about 300 electron volts. Most of the observed X-rays lie between about 0.3 and 1.5 keV, with a small but useful fraction having energies as high as 10 to 100 keV. In a densitometer tracing of a bent crystal spectrograph taken with a KAP crystal, the radiation appears to be mostly lines in the spectral interval of about 0.7 to 1.2 keV. The unusual sharpness of the spectral detail is due to the tiny dimensions of the source.

This novel point source of X-rays provides a spectrum tuneable throughout a range of about 0.1 to 100 keV. This can provide hospitals with revolutionary new X-ray machines for taking ultrasharp, ultrafast radiographs, and for performing swift and precise irradiations of cancer tissue. Indeed, the applications to medical research, diagnosis, and treatment seem virtually endless. A few of the more important applications according to the present invention are discussed below.

In one typical application the soft X-ray output is used to take X-ray photographs. For example, a 8 mm thick section of a dog's heart and a 6 mm thick cancer nodule (carcinoma 255) were taken by placing dessicated samples over dental film at a distance of about 10 cm from the focal spot. Comparison with a radiograph of the same dog heart section taken with a conventional high resolution soft X-ray source (the Picker Hotshot) using a 1 minute exposure shows that the laser photograph not only matches the high resolution of the conventional photograph, but also has the added advantage of a pulse width that is short enough to arrest any biological motion that might occur. The short pulse width of the X-rays makes them also especially adaptable to flash microradiography, with a resolving power of less than a micron being possible.

Another application of the new X-ray source is the soft X-ray irradiation of tumors located on the skin or on the surface of internal organs, thereby effecting the selective destruction of the tumor without injuring underlying tissue. The selective irradiation is made possible by the short mean-free-path of soft X-rays in tissue. A second useful property of soft X-rays (as opposed to hard X-rays) is their large critical angle for total reflection when incident on smooth surfaces such as float glass, etc. The critical angle for float glass is approximately 1.5 degrees at 1 keV, and can be three or four times higher for smooth surfaces of high-Z materials such as tungsten, gold, and platinum. This reflection property has permitted the development of a new device that channels X-rays in much the same way that light is guided by a light pipe, and may conveniently be described as an "X-ray pipe." New types of endoscopes can be constructed based on the X-ray pipe principle. One such device is essentially a conventional bronchoscope except that it contains a glass tube about 8 mm in diameter for channeling the X-rays. A straight piece of tubing about 107 cm long was tested with soft X-rays and was found to deliver about 32 times more Joules per square centimeter than were delivered in a purely line of sight irradiation. A similar experiment was performed with a curved tube, in which case the enhancement dropped to a factor of about 8. Other typical X-ray pipe devices include an "X-ray hypodermic needle" that can be inserted into a subject in the same way as a conventional hypodermic needle is inserted. Another is an "X-ray catheter" consisting of a flexible X-ray pipe that can be run through the arteries to remote locations such as the interior of the heart. These devices have the capability of channeling the X-rays around corners. For sharp angles, where only very soft X-rays can survive the turn, Bragg angle reflection is employed.

The hard X-rays produced with the laser can provide sharper radiographs of the human body, including chest X-rays that stop cardiovascular and respiratory motion, for example. A hard X-ray probe for taking radiographs from special vantage points in the body comprises typically a long narrow hollow cone with a special target on its tip. The cone is inserted in the body and the laser beam is focused through the cone to the target by means of a long focal length lens.

Aside from the radiography applications, the hard X-rays can also play a role in radiotherapy, utilizing the probe described above (which can also deliver soft X-rays), or Bragg angle, critical angle, or Fresnel lens focusing devices can direct the X-rays to small points in the body.

Further details of typical embodiments are provided in the drawings and in the detailed description herein.

SUMMARY OF THE INVENTION

A typical method of applying radiation according to the present invention comprises the steps of producing X-rays of a selected spectrum and intensity, and directing the X-rays to a desired location; the steps comprising more particularly directing radiant energy from a laser onto a target to produce such X-rays at the target, and so positioning the target adjacent to the desired location as to emit the X-rays toward the desired location; or producing such X-rays in a region away from the desired location, and channeling the X-rays to the desired location.

For producing a radiograph, where the desired location is in a living organism, the X-rays typically are provided in a short pulse to avoid any blurring of the radiograph from movement of or in the organism. The duration of the pulse preferably is less than about 1 millisecond. Where the X-rays are directed substantially as from a point source to a subject at the desired location, an image recording means may be positioned behind the subject and spaced therefrom to record an enlarged image of the subject.

For altering tissue, where the desired location is in a living organism, the selected spectrum and intensity preferably are such as to affect substantially the tissue in a preselected volume without injuring nearby tissue. Typically the selected spectrum comprises the range of about 0.1 to 100 keV, and the intensity is selected to provide about 100 to 1000 rads at the desired location.

The X-rays may be produced by stimulated emission thereof, typically in a single direction.

Typical apparatus for applying radiation according to this invention comprises, in combination, means for producing X-rays of a selected spectrum and intensity, and means for directing the X-rays to a desired location; the combination comprising more particularly means for directing radiant energy from a laser onto a target to produce such X-rays at the target, and means for so positioning the target adjacent to the desired location as to emit the X-rays toward the desired location; or means for producing such X-rays in a region away from the desired location, and means for channeling the X-rays to the desired location.

In some embodiments the producing means provides stimulated emission of the X-rays, typically substantially in a single direction.

The radiant energy directing means may be shaped to circumvent any obstruction between the laser and the target. Similarly, the X-ray channeling means may be shaped to circumvent any obstruction between the region where the X-rays are produced and the desired location.

The radiant energy directing means typically comprises a lens and barrier means surrounding the path of the radiant energy between the lens and the target. Typically the barrier means comprises an elongate hollow enclosure and the lens has a focal length approximately equal to the length of the enclosure and a focal ratio of at least about f/3. The enclosure typically is impermeable, with a vacuum inside. The barrier means typically comprises a bend and reflecting means therein to direct the radiant energy around the bend. Where desired, the angle of the bend may be adjustable. Typically one end of the enclosure is attached to the lens and the other end is attached to the target positioning means. The target positioning means typically comprises an impermeable covering member hermetically attached to the enclosure and substantially transparent to the X-rays in a region between the target and the desired location.

The means for producing X-rays in a region away from the desired location typically comprises means for directing radiant energy from a laser onto a target located in the region to produce such X-rays at the target.

The X-ray channeling means typically comprises an elongate hollow guide whose inner surface is substantially reflective to X-rays impinging on it at or below the critical angle. The guide typically comprises a bend and reflecting means such as Bragg angle or critical angle reflectors therein to direct the X-rays around the bend. The guide typically comprises an impermeable enclosure substantially transparent at each end, with a vacuum inside. Where desired, the guide may be flexible.

A plurality of adjacent guides may be provided, typically with the individual guides protruding to different distances at the desired location to distribute the X-rays over a selected volume. The protruding distances may be adjustable.

The apparatus may comprise a filter that effectively blocks substantially all of the X-rays produced above and below a selected wavelength range so that only X-rays in the selected range can reach the desired location. The selected range typically comprises only a single spectral line.

The apparatus may comprise means adjacent to the desired location for receiving the X-rays and scattering them. The scattering typically is substantially omnidirectional. Typical receiving and scattering means comprises a powder consisting essentially of crystalline particles.

BRIEF DESCRIPTION OF THE DRAWINGS

FIG. 1 is a schematic plan view, partly in section, of typical apparatus according to the present invention.

FIG. 2 is an enlarged similar view of an alternative form of the portion of the apparatus in the rectangle 2 in FIG. 1.

FIG. 3 is a schematic view of features useful in some embodiments of the invention.

FIG. 4 is a schematic view of a typical filter that may be used in the invention.

FIGS. 5 and 6 are schematic views illustrating typical uses of the invention.

DESCRIPTION OF PREFERRED EMBODIMENTS

Referring to FIG. 1, typical apparatus for applying radiation according to this invention comprises, in combination, means for producing X-rays of a selected spectrum and intensity, and means for directing the X-rays to a desired location. Where convenient, the combination may comprise more particularly means 10 for directing radiant energy 11 from a laser 12 onto a target 13 to produce such X-rays 14 at the target 13, and means 15 for so positioning the target 13 adjacent to the desired location at 16 as to emit the X-rays 14 toward the desired location 16.

Where preferred, the combination may comprise means, such as 10 (or any other convenient means) for producing such X-rays 14 in a region 16 which is away from the (different) desired location 17, together with means 18 for channeling the X-rays 14 to the desired location 17.

In some embodiments the producing means 10 provides stimulated emission of the X-rays 14, typically substantially in a single direction as indicated at 19.

The radiant energy directing means 10 may be shaped to circumvent any obstruction 21 between the laser 12 and the target 13. Similarly, where the X-ray channeling means 18 is included, it may be shaped to circumvent any obstruction 22 between the region 16 where the X-rays 14 are produced and the desired location 17.

The radiant energy directing means 10 typically comprises a lens 23 and barrier means 24 surrounding the path 25 of the radiant energy 11 between the lens 23 and the target 13. Typically the barrier means comprises an elongate hollow enclosure 24 and the lens 23 has a focal length approximately equal to the length of the enclosure 24 and a focal ratio of at least about f/3. The enclosure 24 typically is impermeable, with a vacuum inside (pressure of about $10^{-4}$ torr or less). The barrier means 24 typically comprises a bend, as at 26, and reflecting means, such as a mirror 27, therein to direct the radiant energy 11 around the bend 26. Where desired, the angle of the bend 26 may be adjustable, as by making the enclosure 24 flexible in the vicinity of the bend 26. Typically one end portion 31 of the enclosure 24 is attached to the lens 23 and the other end portion 32 is attached to the target positioning means 15. The target positioning means 15 typically comprises an impermeable covering member 33 hermetically attached to the enclosure 24 and substantially transparent to the X-rays in a region 34 between the target 13 and the desired location 16.

The means for producing X-rays 14 in a region 16 away from the desired location 17 typically, but not necessarily, comprises means, such as 10, for directing radiant energy 11 from a laser 12 onto a target 13 located in the region 16 to produce such X-rays 14 at the target 13.

The X-ray channeling means 18 typically comprises an elongate hollow guide 41 whose inner surface 42 is substantially reflective, as indicated at 43, to X-rays impinging on it at or below the critical angle. The guide 41 typically comprises a bend, as at 45, and reflecting means 46 or 46', such as Bragg angle reflectors 51 (FIG. 2) or critical angle reflectors, as indicated at 52, therein to direct the X-rays 14 around the bend 45. In FIG. 1 the reflecting means 46 may comprise a smooth surface 52 of any suitable material such as float glass, tungsten, gold, or platinum as required to reflect X-rays 14 of the selected spectrum impinging on the surface 52 at or below the critical angle. In FIG. 2 the alternative form of reflecting means 46' may comprise a single crystal 51 of a suitable material such as potassium acid phthalate (KAP), sodium chloride, or potassium chloride, having a regular arrangement of atoms or molecules 53 in rows and columns as shown in FIG. 2 to provide Bragg angle reflection therefrom, as at 54, of X-rays 14 where the selected spectrum comprises only a single spectral line. Since X-rays of any other wavelength are not reflected in the proper direction, the Bragg angle reflector 46' serves not only as a means for directing X-rays around a bend but also as a narrow band-pass filter.

The hollow guide typically comprises an impermeable enclosure 41 substantially transparent at each end, with a vacuum inside (pressure of about $10^{-4}$ torr or less). Where it is necessary or convenient to bend the guide 41, it may be flexible, as in the lower portion 47.

As shown in FIG. 3, a plurality of adjacent guides 41' may be provided, typically with the individual guides 41' protruding to different distances, as at 64, 65, 66, and 67, at the desired location 17' to distribute the X-rays 14 over a selected volume 68. The protruding distances may be adjustable, as by knobs 69 at threaded overlapping sections 63 of the guides 41'.

The apparatus may comprise a filter 71 (or 46') that effectively blocks substantially all of the X-rays 14 produced above and below a selected wavelength range so that only X-rays in the selected range can reach the desired location 17. The selected range typically comprises only a single spectral line. The filter 71 may be located at an end of the X-ray channeling guide 41, as shown in FIG. 1, or at any other convenient place in the path of the X-rays 14. As is mentioned above in the description of FIG. 2, a Bragg angle reflector 46' may be used to provide the required filtering action. Another type of filter that may be used is a filter 71 as in FIG. 4. X-rays 14 having a broad spectrum as indicated at 72 are directed toward a reflector 73, having a smooth surface at 74, at an angle that is larger than the critical angle for shorter wavelengths than those in the selected range and equal to or less than the critical angle for wavelengths in the selected range or longer. Thus only the longer wavelengths of the X-rays 14 are reflected at 74 to proceed, as indicated at 75, to a transmission foil 76 of such thickness, and having a composition of such internal structure and density, as to be substantially transparent to any spectral line within the selected wavelength range and substantially opaque to spectral lines of longer wavelengths. Thus the filter 71 may be designed to provide only a single spectral line output, as indicated by the pure sine wave at 77; or it may provide a narrow band of spectral lines at the output end 77 when preferred.

The apparatus may comprise means 81 adjacent to the desired location 17 for receiving the X-rays 14 and scattering them. The scattering typically is substantially omnidirectional as indicated (at 81) in FIG. 1. Typical receiving and scattering means 81 comprises a powder consisting essentially of crystalline particles 82. The powder may comprise such materials as potassium acid phthalate (KAP), sodium chloride, potassium chloride, etc., depending on the wavelengths. Typically the interatomic spacings in the materials are of the order of about a wavelength. For substantially omnidirectional scattering, crystals of various sizes and configurations should be used.

A typical method of applying radiation according to the present invention comprises the steps of producing X-rays of a selected spectrum and intensity, and directing the X-rays to a desired location; the steps comprising more particularly directing radiant energy 11 from a laser 12 onto a target 13 to produce such X-rays 14 at the target, and so positioning the target 13 adjacent to the desired location 16 as to emit the X-rays 14 toward the desired location 16; or producing such X-rays 14 in a region 16 which is away from the (different) desired location 17, and channeling the X-rays 14 to the desired location 17.

For producing a radiograph, where the desired location 16 or 17 is in a living organism, the X-rays typically are provided in a short pulse to avoid any blurring of the radiograph from movement of or in the organism. The duration of the pulse preferably is less than about 1 millisecond. As in FIG. 6, where the X-rays 14 are directed from a small target 13', having a diameter of about 10 to 100 microns, and thus substantially as from a point source, to a subject 84 at the desired location, an image recording means such as a film 85 may be positioned as shown behind the subject 84 and spaced therefrom to record an enlarged image of the subject 84. Since the X-rays 14 emanate from substantially a point source they continue in straight line paths, as indicated at 86, after passing through the portions of the subject 84 that are transparent or translucent thereto and thus provide an enlarged image on the X-ray sensitive film 85. The region 87 between the subject 84 and the film 85 should of course be kept free of any matter that is not transparent to the X-rays, as by enclosing the region 87. In some cases, as in microradiography, it may be desirable to stop down the source of the X-rays to an effective diameter even smaller than 10 microns.

For altering tissue, where the desired location 16' or 16" is in a living organism 91, as in FIG. 5, the selected spectrum and intensity preferably are such as to affect substantially the tissue in a preselected volume 68' or 68" at the location 16' or 16" without injuring nearby tissue. Typically the selected spectrum comprises the range of about 0.1 to 100 keV, and the intensity is selected to provide about 100 to 1000 rads at the desired location. The dosage may be provided all at one sitting or in several sittings. The dose at any sitting may comprise one or more pulses. Where the desired location 16' is near surface 92 of the organism 91, the target 13' in the enclosure 24' may be placed against the surface 92 adjacent the preselected volume 68' to emit the X-rays thereto. Where the desired location 68" is deeper inside the organism 91, the enclosure 24" may comprise a very thin end portion 32", straight, curved, or articulated, as required, to penetrate into the desired location 16" and position the target 13" adjacent the preselected volume 68" to emit X-rays thereto.

As is explained in detail in the United States patent application of Mallozzi et al., referred to in the Background section herein, a typical method of producing X-rays for use in the present invention comprises directing radiant energy from a laser onto a target, and high conversion efficiency is obtained by at least one the following steps:

(a) providing the radiant energy in a low-power precursor pulse focused onto the target to generate a plasma and shortly thereafter a higher-power main pulse focused onto the plasma to heat it and thus to produce X-rays therefrom;

(b) focusing the radiant energy onto a target shaped to contain or compress the plasma generated by the energy so as to increase the density of the plasma, to increase its duration in a dense state, or both;

(c) providing the radiant energy in sufficient power to generate a plasma having a low-density region wherein the plasma frequency is less than the laser radiation frequency and a higher-density (overdense) region wherein the plasma frequency is greater than the laser radiation frequency so that the radiant energy is absorbed in the low-density region and conducted into the higher-density region where the bulk of the X-rays are produced;

(d) focusing the radiant energy onto a target containing fusionable material and material capable of producing a substantial quantity of X-rays so as to provide a controlled thermonuclear reaction therein and thus increase the total energy available to produce X-rays.

The target typically consists essentially of an element having a high atomic number Z, i.e., an atomic number Z greater than 10. Typically the target consists essentially of iron, calcium, chromium, nickel, aluminum, lead, tungsten, or gold.

The amplitude, duration, and shape of the precursor pulse typically are adjusted to control the intensity and spectral content of the X-rays. The precursor pulse typically comprises about 0.01 to 5 joules (about $10^{10}$ to $10^{12}$ watts per square centimeter) in about 1 to 30 nanoseconds, and strikes the target at an angle of about 20 to 70 degrees from its surface.

The main pulse typically comprises at least about 0.1 joule in about $10^{-3}$ to 30 nanoseconds, preferably about 10 to 200 joules in about 1 to 3 nanoseconds, and strikes the plasma about 1 to 30 nanoseconds after the precursor pulse strikes the target.

In a typical embodiment, the target consists essentially or iron and the duration of the precursor pulse is about 8 to 10 nanoseconds.

The electron density in the low-density region of the plasma typically is about $10^{16}$ to $10^{21}$ per cubic centimeter, and in the higher-density region about $10^{19}$ to $10^{25}$ per cubic centimeter. The radiant energy typically is focused onto a spot on the target having a diameter of about 10 to 1000 microns. The volume of the plasma typically is about $10^{-6}$ to $10^{-3}$ cubic centimeter, the thickness of the plasma in any direction being about 0.001 to 0.1 centimeter.

For low energy applications the X-rays are emitted predominantly in the form of spectral lines.

The radiant energy may be focused onto a spot on the target having a diameter of about 10 to 100 microns, generating a plasma of about the same diameter, to form substantially a point source of X-rays and thus to provide substantially the advantages of stimulated emission of X-rays.

In some embodiments of the invention the composition of the target and the temperature of the plasma are selected to provide a substantial amount of stimulated emission of X-rays.

In other embodiments X-rays are directed to impinge upon a fluorescent target so as to remove inner shell electrons from atoms thereof and thereby create a population inversion.

In a typical method of providing stimulated emission of X-rays by directing radiant energy onto a target to create by means of a pumping mechanism some upper and lower laser levels, the required population inversion is not established by the pumping mechanism alone, but by the combined action of the pumping mechanism and a quenching mechanism that extinguishes the lower laser level at a rate sufficient to establish and continuously maintain the inversion. The pumping mechanism typically comprises excitation by collisions of electrons and ions or by dielectronic recombination. The quenching mechanism typically comprises Auger transitions, Coster-Krönig transitions, or collisions. The radiant energy may be from a laser, or it may comprise a beam of electrons. The pumping mechanism may comprise a beam of electrons.

In some embodiments the pumping mechanism is sufficient to create a population inversion but not to maintain it.

Where convenient, the radiant energy may be furnished as a pulse having a duration that is less than the lifetime of the upper transition state involved to produce stimulated emission of X-rays from the highly populated levels therein. The upper laser level is metastable in some cases.

For stimulated emission of X-rays, where the radiant energy comprises a pumping pulse having a duration that is longer than the lifetime of the upper state involved, overpopulation of the lower laser level may be avoided by depopulating it faster than it is populated by transitions from the upper laser level and other atomic levels, to maintain continuous wave operation during a substantial portion of the pumping pulse. Typically the lower laser level is depopulated by Auger transitions, Coster-Krönig transitions, or collisions; and the upper laser level is excited by electron-ion collisions, dielectronic recombination, three-body recombination, or photoionization. Typically a beam of X-rays is directed onto a target to remove electrons from an inner shell or subshell by photoionization, then electrons decay from an exterior shell or subshell filling the holes in the inner shell or subshell and leaving holes in the exterior shell or subshell, the holes in the exterior shell or subshell are then filled by Auger or Coster-Krönig transitions from more exterior shells or subshells, thereby eliminating the lower laser states and decreasing the population in the lower laser level. In some embodiments a beam of X-rays is directed onto a target comprising essentially a material having an atomic number Z less than about 40 to remove K-shell electrons by photoionization, the electrons decay from the L shell filling the holes in the K shell and leaving holes in the L shell, the holes in the L shell are then filled by Auger transitions from the M and N shells or Coster-Krönig transitions from other subshells of the L shell, thereby eliminating the lower laser states and decreasing the population in the lower laser level.

Laser action can be obtained where the radiant energy is focused onto a substantially rectangular spot on the target having a length at least about ten times its width to generate a plasma substantially in the shape of an elongate cylinder that forms a source of spontaneously emitted X-rays and amplifies them by the process of stimulated emission therein predominantly in the directions of its axis. The spot typically is about 1 to 100 microns wide and about 100 to $10^5$ microns long, and the cylindrical plasma that is generated is about 1 to 1000 microns in diameter and about 100 to $10^5$ microns long.

Laser action can be provided where an amplifying cavity is positioned adjacent the plasma to receive a substantial proportion of the X-rays produced and by multiple reflections to direct the X-rays repeatedly through the cavity and the plasma to amplify them and to direct the coherent amplified waves predominantly in a predetermined path. A typical amplifying cavity comprises a hollow guide that is substantially circular in cross section and due to reflection at or below the critical angle has a substantially completely reflective side surface. In a typical embodiment the guide comprises a pair of coaxial substantially circular cylinders of which one end of each is substantially completely reflective (as by having an appropriately arranged configuration which employs critical angle or Bragg diffraction processes) and the other end is positioned adjacent to the plasma. In another the guide comprises substantially a torus having a gap therein in the shape of a thin disk substantially coaxial therewith, and the plasma is positioned in the gap.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. Apparatus for applying X-rays at a desired location, comprising
    means for positioning a target in a region away from the desired location;
    means for directing radiant energy from a laser onto the target to produce X-rays of a selected spectrum and intensity at the target; and
    means for channeling the X-rays to the desired location comprising an elongate hollow guide whose inner surface is substantially reflective to X-rays impinging on it at or below the critical angle, wherein the inner surface of the hollow guide is a smooth surface comprising essentially float glass, tungsten, gold, platinum, or similar high-Z material, having a critical angle of at least about 1.5 degrees at 1kev.

2. Apparatus as in claim 1, wherein the X-ray channeling means is shaped to circumvent any obstruction between the region where the X-rays are produced and the desired location.

3. Apparatus as in claim 1, wherein the guide comprises a bend and reflecting means therein to direct the X-rays around the bend.

4. Apparatus as in claim 3, wherein the reflecting means comprises Bragg angle or critical angle reflectors.

5. Apparatus as in claim 1, wherein the guide comprises an impermeable enclosure substantially transparent at each end, with a vacuum inside.

6. Apparatus as in claim 1, wherein the guide is flexible.

7. Apparatus as in claim 1, comprising a plurality of adjacent guides, with the individual guides protruding to different distances at the desired location to distribute the X-rays over a selected volume.

8. Apparatus as in claim 7, wherein the protruding distances are adjustable.

* * * * *